(12) United States Patent
Bae et al.

(10) Patent No.: US 6,465,671 B1
(45) Date of Patent: Oct. 15, 2002

(54) SILANE COUPLING AGENT AND METHOD FOR PREPARING THE SAME

(75) Inventors: Byeong Soo Bae, Taejeon (KR); Yoon Ki Choi, Taejeon (KR); Young Joo Eo, Taejeon (KR); Oun Ho Park, Taejeon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 09/480,302

(22) Filed: Jan. 10, 2000

(30) Foreign Application Priority Data

Jan. 23, 1999 (KR) .............................................. 99-2073

(51) Int. Cl.$^7$ ................................ C07F 7/10; C07F 7/08
(52) U.S. Cl. ...................... 556/413; 556/436; 556/427; 556/445; 556/418; 556/423; 556/438; 556/440; 549/214; 549/215
(58) Field of Search ................................ 556/413, 436, 556/427, 445, 418, 423, 438, 440; 549/214, 215

(56) References Cited

U.S. PATENT DOCUMENTS

| | | | |
|---|---|---|---|
| 4,262,067 A | 4/1981 | Philipp et al. ............... | 429/139 |
| 4,416,938 A | 11/1983 | Haskell ....................... | 428/289 |
| 5,496,649 A | 3/1996 | Mallory et al. ............. | 428/518 |
| 5,512,338 A | 4/1996 | Bianchini et al. .......... | 428/35.4 |
| 5,547,764 A | 8/1996 | Blais et al. ................. | 428/461 |
| 5,604,042 A | 2/1997 | Bianchini et al. ........... | 428/507 |
| 6,043,331 A | * 3/2000 | Herzig ........................ | 556/445 |

FOREIGN PATENT DOCUMENTS

WO 94/07947 4/1994

OTHER PUBLICATIONS

Ashby, E.C., et al., "Organometallic Reaction Mechanisms. X. Concerning the Effect of Magnesium Metal Purity and the Method of Preparation of Grignard Reagents on Reaction with Ketones and Nitriles." Journal of the American Chemical Society, vol. 95, No. 10, pp. 3330–3337, 1973.
Berk, Scott C., et al., "An Air–stable Catalyst System for the Conversion of Esters to Alcohols." Journal of Organic Chemistry, vol. 58, No. 11, 1993, pp. 3221–3222.
Berk, Scott C., et al. "An Air–Stable Catalyst System for the Conversion of Esters to Alcohols." The Journal of Organic Chemistry, vol. 57, No. 14, pp. 3751–3753, 1972.
Bonnemann, Helmut, et al. "The Preparation of Finely Divided Metal Powders and Transition Metal Complexes using "organically solvated" magnesium." Journal of Organometallic Chemistry, 451 (1993) pp. 23–31.
Coumbe, Tristan, et al. "Titanium (IV) Catalysis in the Reduction of Phosphine Oxides" Tetrahedron Letters, vol. 35, No. 4, pp. 625–628, 1994.

Gilman, Henry, et al., "A Simplified Preparation of Activated Magnesium for Grignard Reagents." pp. 577–583.
Greene, Theodora W., et al. "Protection for the Hydroxyl Group, Including 1,2–and 1,3–Diols," *Protective Groups in Organic Synthesis*, $2^{nd}$ Ed., John Wiley & Sons, Inc. pp. 10–223.
Kocienski, Philip J. "Diol Protecting Groups," *Protecting Groups*, Georg Thieme Verlag Stuttgart, New York, 1994 pp. 94–185.
Lai, Yee–Hing, "Grignard Reagents from Chemically Activated Magnesium," Sythesis, pp. 585–604, 1981.
Moriwake, Tosio, "The Reformatsky Reaction. I. Condensation of Ketones and t–Butyl Bromoacetate by Magnesium," vol. 31, pp. 983–985, Mar. 1966.
Oppolzer, Wolfgang, et al. "Efficient Preparation of Allylic Grignard Reagents Using Slurries of Precondensed Magnesium" Tetrahedron Letters, vol. 23, No. 38, pp 3901–3904, 1982.
Pearson, D.E., et al., "A Study of the Entrainment Method for Making Grignard Reagents", vol. 24, pp. 504–509, Apr., 1959.
Speier, John L., et al. "The Addition of Silicon Hydrides to Olefinic Double Bonds. Part II. The Use of Group VIII Metal Catalysts.", pp. 974–979, Feb. 20, 1957.
Wolkoff, Peder, "Dehydrobromination of Secondary and Tertiary Alkyl and Cycloalkyl Bromides with 1,8–Diazabicyclo [5.4.0]undec–7–ene. Synthetic Applications" Journal of Organic Chemistry vol. 47, pp. 1944–1948, 1982.
Xiiong, Heping, "Facile Formation of Substituted 2–Butene–1,4–diylmagnesium Using Highly Reactive Magnesium: A Simple Approach to Complex Carbocycles and Functionalized Ketones." The Journal of Organic Chemistry, vol. 54, No. 14, pp. 3247–3249, 1989.

* cited by examiner

*Primary Examiner*—Paul F. Shaver
(74) *Attorney, Agent, or Firm*—Madson & Metcalf

(57) ABSTRACT

Disclosed herein are a silane coupling agent and a method of preparing the same useful for a composite organic-inorganic material. The silane coupling agent is represented by the formula of $R_1R_2R_3Si$—X, wherein $R_1$, $R_2$, and $R_3$, respectively, represent straight or branched alkyl having 4 to 22 carbon atoms, alkoxy, phenyl, phenyl alkoxy, benzyloxy or phenyl alkyl group. The method comprises the steps of: dissolving a vinyl derivative in a solvent under a nitrogen or argon atmosphere; and reacting the resulting solution with an alkoxysilane derivative at a temperature of 20 to 200° C. for 1 to 72 hours in the presence of a metal catalyst. Alternatively, the method comprises the steps of: dissolving alkylmagnesium halide in a solvent under a nitrogen or argon; and reacting the resulting solution with haloalkoxysilane at a temperature of –78° C. to 50° C. for 0.1 to 5 hours.

5 Claims, 5 Drawing Sheets

SILANE COUPLING AGENT AND METHOD FOR PREPARING THE SAME

BACKGROUND OF THE INVENTION

1. Field of the Invention

The present invention relates in general to ac silane coupling agent and a method for the preparing the same by which an organic material and an inorganic material can be covalently bonded to each other. More particularly, the present invention relates to a silane coupling agent useful for the preparation of a composite material of a silicone oxide and an alcohol group-containing polymer, such as polyvinyl alcohol, ethylene-vinyl alcohol copolymer, tetrafluoroethylene-vinylalcohol copolymer, or poly (vinylbutyral-vinylalcohol-vinylacetate) copolymer.

2. Description of the Prior Art

A silane coupling agent has a trialkoxysilyl group and an organic functional group which is an acetal or dioxoranyl group. The trialkoxysilyl group is reacted with silanol present in the surface of an inorganic material, such as silicate, whereas the acetal or dioxiranyl group is reacted with a hydroxy group which is a functional group of an organic material. Consequently, they serve to connect the organic material and the inorganic material to each other.

In a composite inorganic-organic material, the most problematic factor is the compatibility between the organic material and the inorganic material. Where such a compatibility is insufficient, the phase separation between the organic and inorganic materials occurs, thus deteriorating physical properties of the composite material.

Meanwhile, in the composite material of the organic material and the inorganic material, the compatibility can be enhanced when the two materials are bonded by a hydrogen bond or other chemical bond. However, the composite material can not be enhanced in a moisture barrier property by only the hydrogen bond.

U.S. Pat. Nos. 5,604,042 and 5,512,338, to which the present invention is related, describes coating the surface of a polyurethane, polyethylene or polyethylene terephtalate film with a solution containing polyvinyl alcohol reacted with melamine-formaldehyde, thereby enhancing an oxygen barrier property of the resulting film structure. Moreover, to improve the moisture barrier property of the film structure, the solution-coated surface is adhered with a cellulose or polyvinylidene chloride film.

In addition, U.S. Pat. Nos. 5,547,764, 5,496,649, 4,416, 938, and 4,262,067 describe crosslinking a hydroxy group in polyvinyl alcohol with aldehyde using glyoxal, or glutaric dialdehyde, thereby improving the oxygen barrier property of the resulting film structure. In this case, even if the hydroxy group in polyvinyl alcohol is reacted with aldehyde to form an acetal group, the formed acetal group can serve as a coupling agent between polyvinyl alcohol polymer chains.

Furthermore, PCT Publication WO 94/07947 describes reacting tetraalkoxysilane with polyvinyl alcohol in the presence of formic acid to form a Si—O—Si bond and also to couple the hydroxy group with the formic acid, thereby improving toughness. However, the latter reference describes that a Si—O—C bond is not formed in the reaction of tetraalkoxysilane and polyvinyl alcohol, and polyvinyl alcohol is dispersed in tetraalkoxysilane. That is to say, the resultant product is not a composite organic-inorganic material, but consists of an organic material dispersed in the inorganic material. Where such a mixture is allowed; to be stand in water for an extended period of time, a fine phase separation between the organic material and the inorganic material may occur in the mixture, thereby deteriorating physical properties of the mixture.

SUMMARY OF THE INVENTION

It is an object of the present invention to improve the compatibility, that is a basic problem with the composite organic-inorganic material, and to prepare a silane coupling agent containing an organic functional group, which is an acetal group or a dioxoranyl group, by reacting a vinyl derivative with an alkoxysilane derivative, or by reacting alkylmagnesium halide with haloalkoxysilane.

A silane coupling agent in accordance with the present invention is prepared by one of the following two methods. A first method comprises the steps of dissolving a vinyl derivative represented by the following formula II in an organic solvent under a nitrogen or argon atmosphere, and reacting the resulting solution with an alkoxysilane derivative represented by the following formula III in the presence of a metal catalyst to produce a silane coupling agent represented by the following formula I. A second method comprises the steps of dissolving alkyl magnesium. halide represented by the following formula IV in a solvent under a nitrogen or argon atmosphere, and reacting the resulting solution with haloalkoxysilane represented by the following formula V to produce a silane coupling agent represented by the following formula I:

  (I)

  (II)

  (III)

$R_1R_2R_3Si$—Z  (IV)

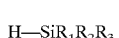  (V)

wherein $R_1$, $R_2$, and $R_3$, respectively, represent straight or branched alkyl having 4 to 22 carbon atoms, alkoxy, phenyl, phenylalkoxy, benzyloxy or phenylalkyl group, each of these groups being optionally substituted with a functional group, such as fluoride, glycidyloxy, amine, vinyl, (meth)acetyl, amino or mercapto group, with the proviso that at least one of $R_1$, $R_2$, and $R_3$ contain an alkoxy group;

X is an alkyl or aryl alkyl group having 4 to 22 carbon atoms, each of these groups being substituted with at least one functional group selected from dioxoranyl, dioxanylalkyl, ketal, alkylideneketal, cycloalkylidenekatal, acetal, dialkylacetal, alkylideneacetal, phenylalkylideneacetal, benzylideneacetal, ketone, and cycloacetal having 4 to 8 carbon atoms and optionally containing, in its carbon chain, at least one atom selected from oxygen, sulfur and nitrogen;

$Y_1$ is an alkyl or arylalkyl group having 4 to 19 carbon atoms, each of these groups being substituted with at least one functional group selected from dioxoranylalkyl, dioxanylalkyl, ketal, acetal, dialkylacetyl, alkylideneacetal, phenylalkylideneacetal, benzylideneacetal, ketone, aldehyde and cycloacetal having 4 to 8 carbon atoms and optionally containing, in its carbon chain, at least one atom selected from oxygen, sulfur and nitrogen;

$Y_2$ has a definition identical to that of $Y_1$, or may contain hydrogen atom; and Z is selected from F, Cl, Br, and I.

The metal catalyst used in accordance with the method of the present invention includes a complex compound in which a central metal is Pt, Ir, Os, Au, or As, and a ligand is H, F, Cl, Br, I, $PPh_3$, $C_5H_5$, CO, OH, $C_2H_4$, $CH_3$, $PCH_3$, $Si(CH_3)_3$, $C_5H_4(CH_3)$, $C_5H_3(CH_3)_2$, $C_5(CH_3)_5$, 1,5-cyclooctadiene, norbornadiene, $C_6H_5$, $CH_2$-t-Bu, acetylacetonato and a combination of two or more of these compounds.

BRIEF DESCRIPTION OF THE DRAWINGS

Other objects and aspects of the invention will be apparent from the following description of embodiments with reference to the accompanying drawings, in which.

DETAILED DESCRIPTION OF THE PREFERRED EMBODIMENTS

Figure 1:
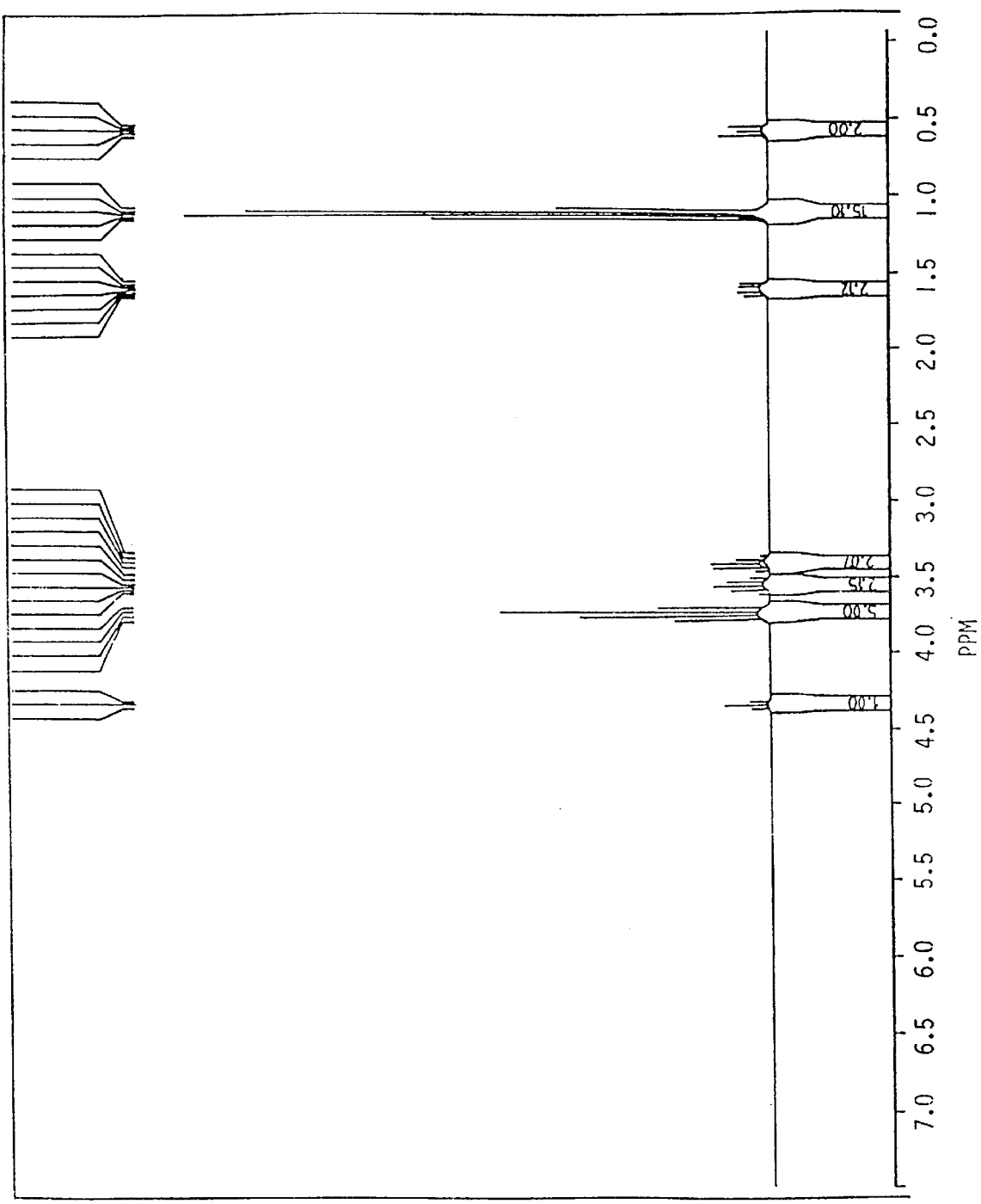
FIG. 1 shows a $^1$H-NMR graph of a silane coupling agent prepared according to Example 4 of the present invention, as measured after dissolving the coupling agent in $CDCl_3$.

The foregoing and other objects, features and advantages of the invention will be apparent to those skilled in the art to which the present invention relates from reading the following specification.

A silane coupling agent represented by the formula I in accordance with the present invention can be prepared by two methods. A first method comprises dissolving a vinyl derivative represented by the formula II and an alkoxysilane derivative represented by the formula II in an organic solvent under a nitrogen or argon atmosphere, and then allowing the resulting solution to be reacted in the presence of a metal catalyst.

Examples of the organic solvent used in accordance with the first and second methods of the present invention include lower alcohol having 1 to 10 carbon atoms, α-methylnaphtalene, methoxynaphtalene, chloronaphtalene, diphenylethane, ethyleneglycol, quinoline, benzene, nitrobenzene, chlorobenzene, bromobenzene, o-dichlorobenzene, toluene, dichlorotoluene, xylene, chloroform, dichloromethane, tetrachlorocarbon, hexane, cyclohexane, heptane, octane, pentane, pyridine, dioxane, tetrahydrofuran (THF), furan, 2-methyl tetrahydrofuran, tetrahydropyran, pyrrole, dibromomethane, tetrachloroethane, 1,2-dichloroethane, 3-nitro-α,α,α-trifluorotoluene, diethylether, and petroleum ether.

Examples of the metal catalyst used in accordance with the present invention include platinum, hydrogen hexachloroplatinate ($H_2PtCl_6$, commercially available from Aldrich, Co.), hydrogen hexabromoplatinate ($H_2PtBr_6$, commercially available from Aldrich, Co.), hydrogen tetrachlororate (HauCL$_4$, commercially available from Aldrich, Co.), hydrogen hexafluoroarsenate (HAsF$_6$, commercially available from Aldrich, Co.), hydrogen hexachloroirridate ($H_2IrCl_{61}$ commercially available from Aldrich, Co.), hydrogen hexachloroosmate ($H_2OsCl_6$, commercially available from Aldrich, Co.), and those prepared by the known method (J. L. Speier, J. A. Webster, G. H. Barnes, J. Am. Chem. Soc., 1957, 79, 974). The reaction in accordance with the first method of the present invention is carried out by adding the metal catalyst, and preferably platinum catalyst, in the amount of 1 to 1,000 ppm, to the solution containing the vinyl derivative and the alkoxysilane derivative, stirring the resulting solution at room temperature, then heating the stirred solution at a temperature of 25 to 200° C., and preferably 50 to 130° C., for 1 to 96 hours, and preferably 3 to 48 hours.

Examples of the vinyl derivative compound used in accordance with the first method of the present invention include acroleindimethylacetal commercially available from Aldrich, Co., 3-butenaldiethylacetal commercially available from Aldrich, Co., those prepared using acrolein by a known method (Theodora W. Greene and Peter G. M. Wuts, "Protective Group In Organic Synthesis", 2nd Ed., John Wiley & Sons, Inc., New York, 1991, Chap. 2–4; Philip J. Kocienoski, "Protecting Groups", Thieme Medical Publishers, Inc., New York, 1994, Chap. 3–5), and those prepared from 2-(2-bromoethyl-)-1,3-dioxane by a known method (Peder Wolkoff, J. Org. Chem., 1982, 47, 1944).

Examples of the alkoxysilane derivative compound represented by the formula which is used in accordance with the first method of the present invention include trialkoxysilane commercially available from Aldrich, Co., and those synthesized by known methods (Tetrahedron Lett., 35,625, 1994; JOC, 57, 3221, 1993; and JOC, 57, 3751, 1992).

A second method for preparing a silane coupling agent represented by the formula I in accordance with the. present invention comprises dissolving haloalkoxysilane represented by the formula V, in the solvent mentioned above regarding the first method, and preferably tetrahydrofuran (THF) or diethyl ether, at a temperature of −78° C. to 50° C. under a nitrogen or argon atmosphere, slowly adding alkylmagnesium, halide represented by the formula IV to the resulting solution via a canula, and then allowing the resulting mixture to be reacted at a temperature of −78° C. to 50° C. for 0.1 to 10 hours, and preferably 0.5 to 2 hours.

The alkylmagnesium halide represented by the formula V can be prepared using 2-(2-bromoethyl)-1,3-dioxorane according to known method (Moriwaki, T., JOC 1996, 31, 983; and Xiong, H., and Rieke, R. D., JOC 1989, 54, 3274). Magnesium necessary in such known methods can be commercially available, or can be prepared according to known methods (Lai, Y. H., Synthesis 1981, 8, 585; Gilman, H., and Kirby, R. H., RTC 1935, 54, 557; Pearson, D. E., Cowan, D., and Beckler, J. D., JOC 1959, 34, 504; Ashby, E. C., Neumann, H. M., Walker, F. W., and Laemmle, J., and Chao, L. C., JACS 1973, 95, 3330; Oppolzer, W., Kuendig, E. P., Bishop, P. M., and Perret, C., TL 1982, 23, 3901; Boennemann, H., Bogdanovic, B., Brinkmann, R., Spliethoff, B., and He, D. W., JOM 1993, 451, 23).

Examples of the compound represented by the formula V, which is used in the second method of the present invention, include chlorotrimethoxysilane commercially available from Aldrich, Co., chlorotriethoxysilane commercially available from Aldrich, Co., chlorotris (1,3-dimethylbutoxysilane) commercially available from Aldrich, Co, and that prepared by a known method (Mater., 4, 1217, 1992).

In the formulas I to V as described above, the definition "substituted or unsubstituted, straight or branched alkyl group" includes, for example, hydrocarbon group, such as methyl, ethyl, n-propyl, isopropyl, n-butyl, isobutyl, sec-butyl, t-butyl, n-pentyl, isopentyl, neopentyl, 1,2-dimethylpropyl, n-hexyl, cyclohexyl, 1,3-dimethylbutyl, 1-isopropylpropyl, 1,2-dimethylbutyl, n-heptyl, 1,4-dimethylpentyl, 2-methyl-1-isopropyl, 1-ethyl-3-methylbutyl, n-octyl, 2-ethylhexyl, 3-methyl-1-isopropylbutyl, 2-methyl-1-isopropylbutyl, 1-t-butyl-2-methylpropyl, or n-nonyl group; alkoxyalkyl group, such as methoxymethyl, methoxyethyl, ethoxyethyl, propoxyethyl, butoxyethyl, methoxyethoxyethyl, ethoxyethoxyethyl, dimethoxymethyl, diethoxyethyl, dimethylethoxy, or diethoxyethyl group; halogenated alkyl group, such as chloromethyl, 2,2,2-trichloromethyl, trifluoromethyl, or 1,1,1,3,3,3-hexafluoro-2-propyl group; and alkoxy group, such as methoxy, ethoxy, n-propoxy, isopropoxy, n-butoxy, sec-butoxy, or t-butoxy.

The following examples are for illustration purposes only and in no way limit the scope of this invention.

EXAMPLE 1

Preparation of 3,3-diethoxy-1-propene

After 10 ml of acrolein commercially available from Aldrich, Co. is dissolved in 50 ml of anhydroust ethanol, 19 ml of triethylorthoformate and p-toluene sulfonic acid are added to the solution, and the resulting mixture is allowed to reflux under a nitrogen atmosphere for 5 hours. After that, the resulting solution is cooled to a temperature of 5° C., extracted with diethyl ether, washed with 5% sodium bicarbonate (NaHCO3) aqueous solution, dried with anhydrous magnesium sulfate ($MgSO_4$), and then evaporated under a reduced pressure to remove ethanol. Next, the material is fractionally distilled, thereby giving 8.4 g of 3,3-diethoxy-1-propene.

Yield: 48%; $^1$H-NMR($CDCl_3$, 300MHz) δ 6 1.41(t, 6H), 3.43(q, 2H), 3.57(q, 2H), 4.79(d, 1H), 5.20(d, 1H), 5.31(d, 1H); MS(m/z, relative intensity): 129($M^+$–1, 27).

EXAMPLE 2

Preparation of 2-vinyl-1,3-dioxane 1 ml of 2-(2-bromoethyl)-1,3-dioxane commercially available from Aldrich, Co., 1.12 ml of 1,8-diazadicyclo [5, 4, 0]undec-7-en (DBU), and 1.12 mg of hydroquinone are added to tetrahydrofuran (THF), and the resulting mixture is. left to react at a temperature of 90° C. under atmospheric pressure for 16 hours. The resulting material is purified by column chromatography (ethylacetate: hexane=1:19(v/v%)), thereby giving 0.19 g of yellowish 2-vinyl-1,3-dioxane. Yield: 23% $^1$H-NMR($CDCl_3$, 300 MHz) δ 2.10(m, 2H), 3.59(t, 2H), 3.74(t, 2H), 3.94(d, 1H), 5.14(d, 1H), 5.24(d, 1H), 5.87(m, 1H); MS(m/z, relative intensity): 113 ($M^+$–1, 43).

EXAMPLE 3

Preparation of 2-(3-butenyl)-1,3-dioxane

After 2.6 ml of 2-(2-bromoethyl)-1,3-dioxane commercially available from Aldrich, Co. is dissolved in 50 ml of tetrahydrofuran, the solution is maintained at a temperature of –78° C., and 20 ml of vinyl magnesiumbromide (1.0M/THF) is slowly added dropwise to the solution. The mixture is allowed to stand at room temperature under atmospheric pressure for 2 hours, and to react at room temperature for 16 hours. The reaction is stopped with 50 ml of methalol, and the solution is added to 200 ml of distilled water. The resulting material is extracted with ethyl acetate three times, dried with anhydrous $MgSO_4$, and then purified by column chromatography (ethylacetate: hexane=1:19(v/v%)), thereby giving 0. 9 g of yellowish 2-(3-butenyl)-1,3-dioxane.

Yield: 34%; $^1$H-NMR($CDCl_3$, 300 MHz) δ 1.45–2.06(m, 6H), 3.73(t, 2H), 4.06(m, 2H), 4.47(t, 1H), 4.87–4.96(m, 2H), 5.58(m, 1H); MS (m/z, relative intensity) : 143($M^+$–1, 15).

EXAMPLE 4

Preparation of 3,3-diethoxypropyltriethoxysilane

Figure 2:
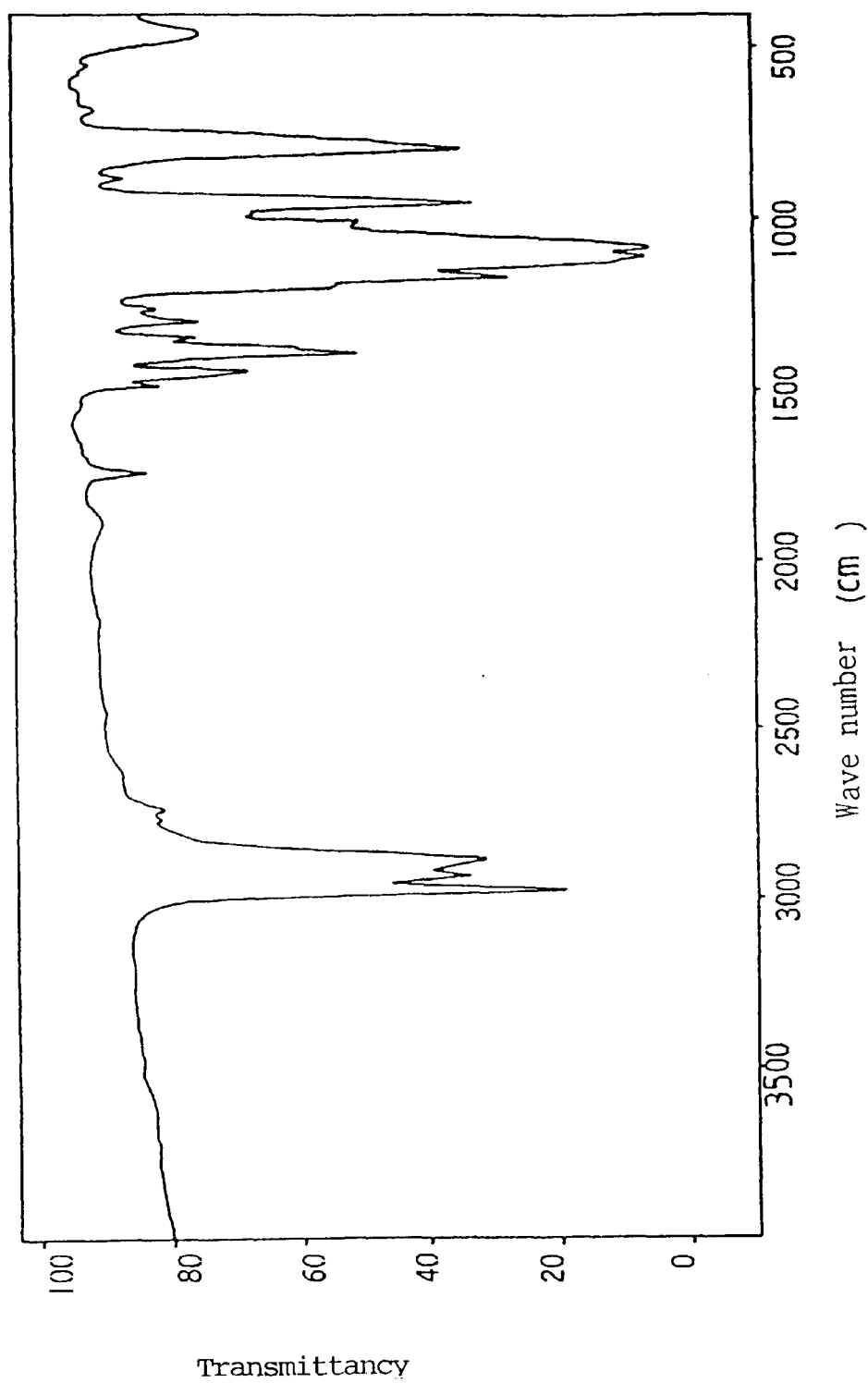
FIG. 2 shows an infrared-absorbing spectrum graph of a silane coupling agent prepared according to Example 4of the present invention.
Figure 3:
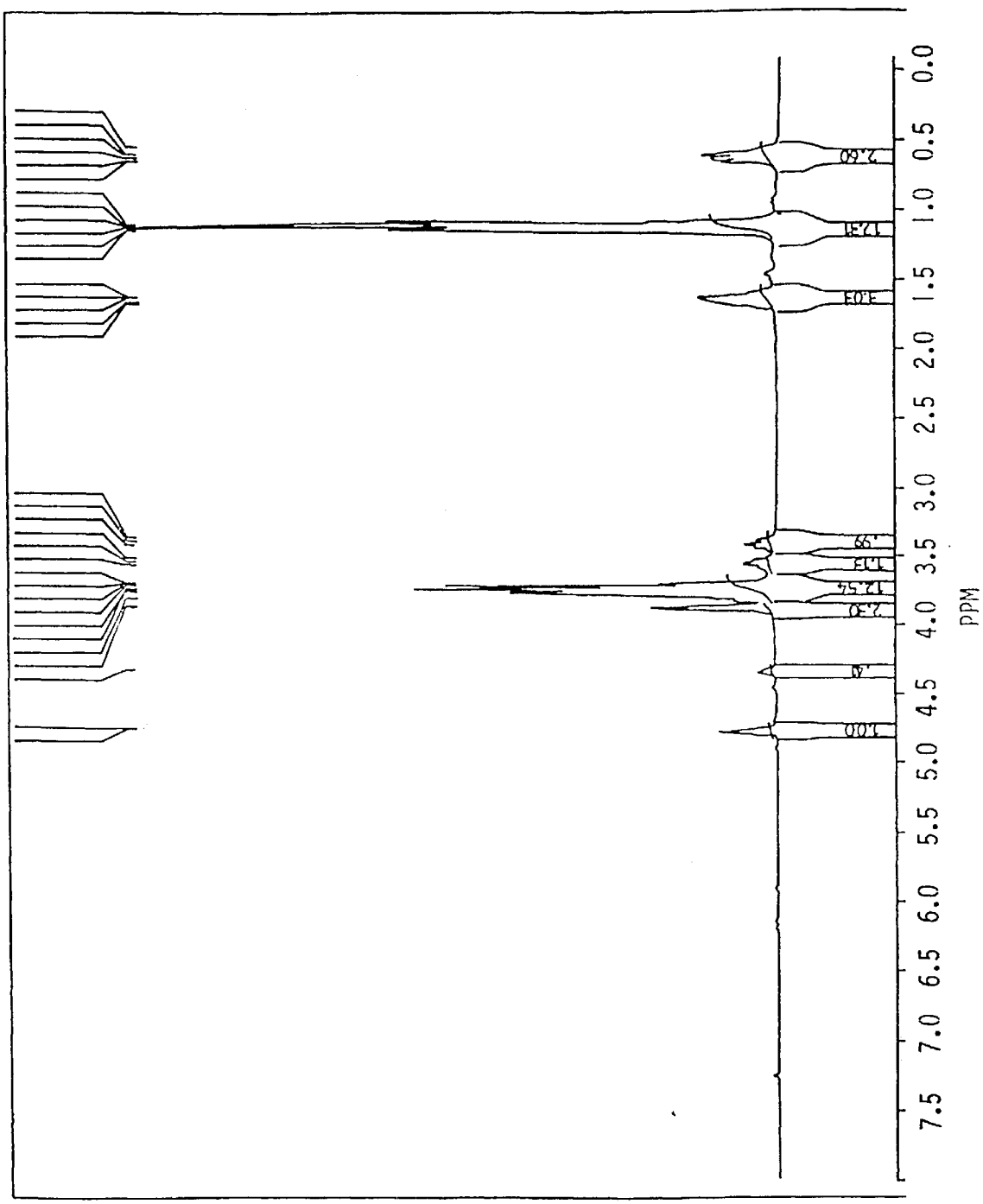
FIG. 3 shows a $^1$H-NMR graph of a silane coupling agent prepared according to Example 5 of the present invention, as measured after dissolving the coupling agent in $CDCl_3$.

A round-bottomed flask is introduced with 2 g (1.1 equivalent) of 3,3-diethoxy-1-propene produced in Example 1, and 2 ml (1 equivalent) of triethoxysilane commercially available from Aldrich, Co. Then, hydrogen hexachloroplatinate ($H_2PtCl_6$), a metal catalyst, is added in the amount of 1 ppm to the solution. After that, the resulting mixture is allowed to react at 100° C. under atmospheric pressure for 48 hours. Next, the resulting material is fractionally distilled under a vacuum, thereby giving 4.2 g of colorless 3,3-diethoxyprophyltriethoxysilane. The product is dissolved in $CDCl_3$ and measured for $_1$NMR and infrared-absorbing spectrum. Results are shown in FIGS. 1 and 2.

Yield: 93%; Infrared-Absorbing Spectrum(neat liquid, $cm^{-1}$); 1167(C—O—C bond), 1106, 1082(Si-O-C bond), 792(Si—C bond); $^1$H-NMR($CDCl_3$, 300 MHz) δ 6 0.58(t, 2H), 1.09–1.16(m, 15H), 1.62(m, 2H), 3.41(q, 2H), 3.56(q, 2H), 3.73(q, 6H), 4.33(t, 1H); $^{13}$C-NMR δ 4.96, 15.18, 18.13, 26.89, 58.20, 60.94, ;104.30; MS(m/z, relative intensity): 293($M^+$–1, 7).

EXAMPLE 5

Preparation of 2-((1,3-dioxorane)-2-yl)-ethyltriethoxysilane

After 2.20 g (1 equivalent) of chlorotriethoxysilane commercially available from Aldrich, Co. is dissolved in 30 ml of tetrahydrofuran at room temperature, the solution is maintained at a temperature of –78° C. 2 g (1 equivalent) of 2-(2-bromoethyl)-1,3-dioxorane is dissolved in 30 ml of tetrahydrofuran under a nitrogen atmosphere, and 0.35 g (1.3 equivalent) of magnesium and 60 mg of iodine are then added. Thereafter, the mixture is allowed to reflux slowly for 2 hours, and the firstly prepared solution maintained at –78° C. is then slowly added dropwise via a canula to the refluxed mixture. Next, the resulting material is allowed to react at –78° C. for 30 minutes and then allowed to be reacted for 1 hour while left stand to increase in temeprature to room temperature.

Figure 4:
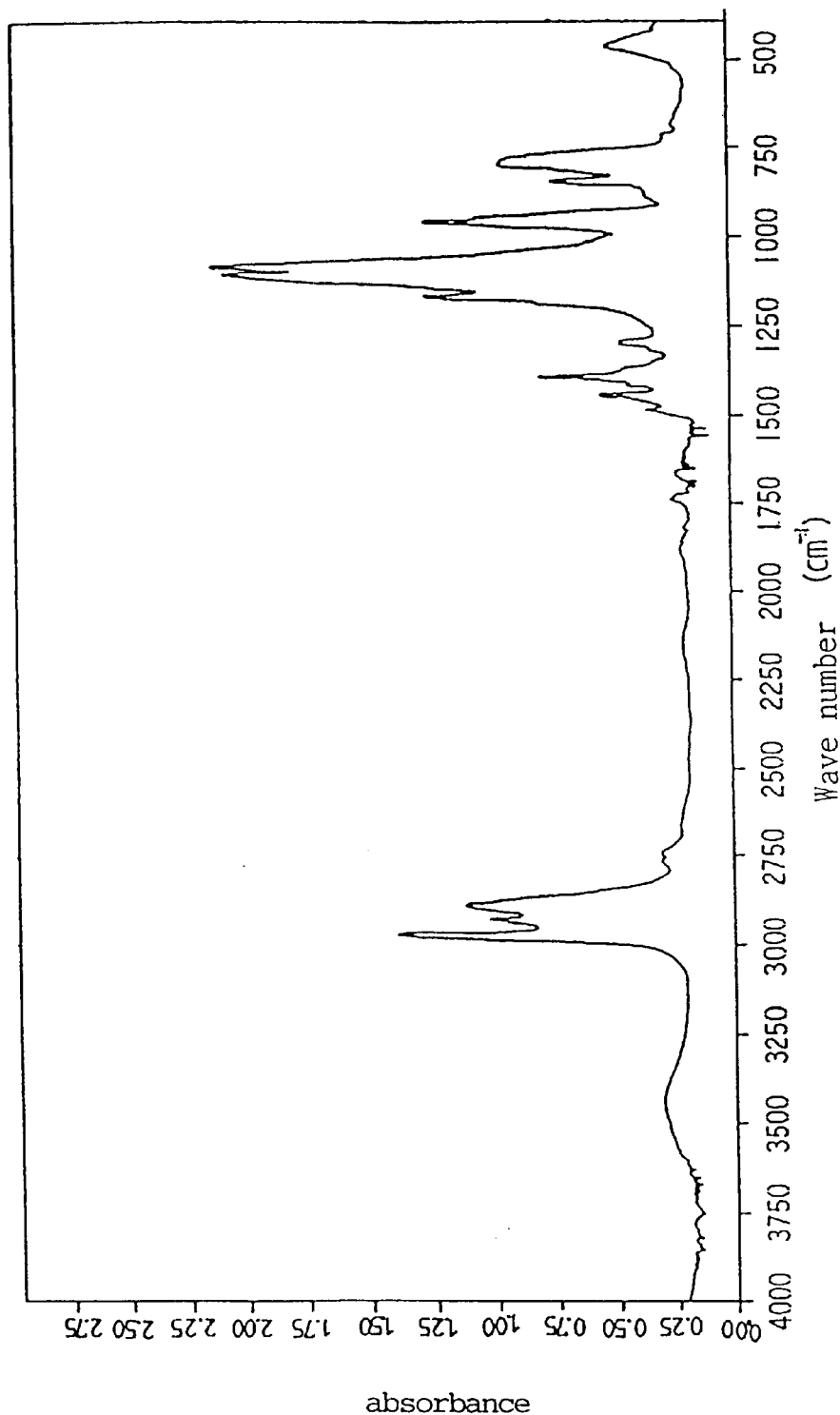
FIG. 4 shows an infrared-absorbing spectrum graph of a silane coupling agent prepared according to Example 5 of the present invention.
Figure 5:
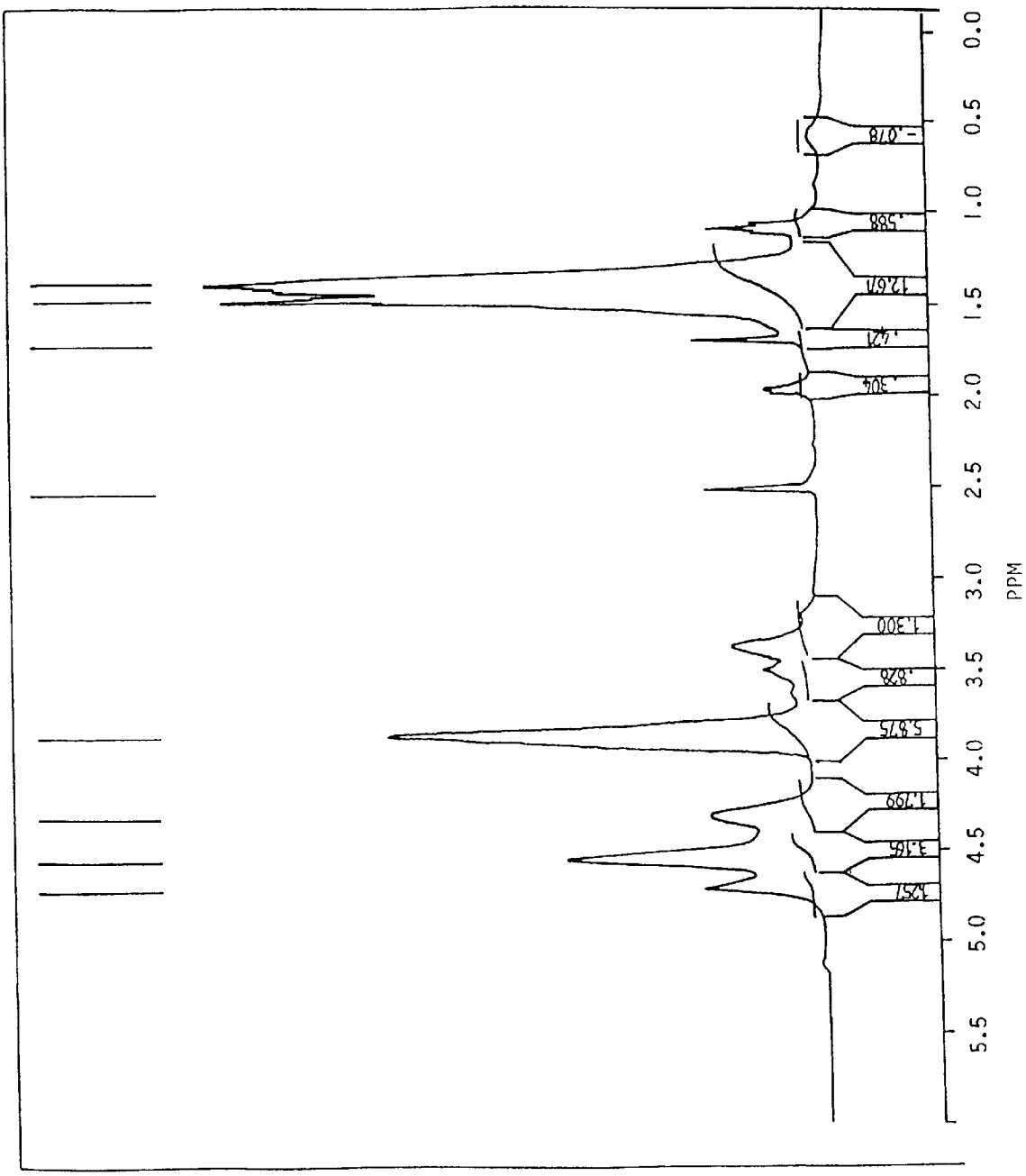
FIG. 5 shows a $^1$H-NMR graph of a composite polyvinyl alcohol-silane coupling agent prepared according to Example 9 of the present invention, as measured after dissolving the composite material in DMSO-$d_6$.

After the reaction is stopped with methanol, the material is washed with 100 ml of distilled water three times to remove a salt. Then, the material is dried with magnesium sulfate, and evaporated under a reduced pressure to remove tetrahydrofuran. Next, the material is fractionally distilled, thereby giving 1.78 g of colorless 2-((1,3-dioxorane)-2-yl)-triethoxysilane. The product is dissolved in $CDCl_3$ and measured for NMR and infrared-absorbing spectrum. Results are shown in FIGS. 4 and 5.

Yield: 61%; Infrared-Absorbing Spectrum(neat liquid, cm$^{-1}$); 1168 (C—O—C bond), 1104, 1010(Si—O—C bond), 796(Si—C bond); $^1$H-NMR(CDCl$_3$, 300 MHz) δ 0.63(t, 2H), 1.11–1.16(m, 9H), 1.65(q, 2H), 3.40(q, 1H), 3.55(q, 1H), 3.70–3.87(m, 8H), 4.76(t, 1H); $^{13}$C-NMR δ 3.87, 15.19, 18.13, 27.14, 58.22, 60.94, 105.45; MS(m/z, relative intensity): 263(M$^+$–1, 18).

EXAMPLE 6

Preparation of 4,4-diethoxybutyltriethoxysilane 4,4-diethoxybutyltriethoxysilane is prepared using the same method as that of Example 4 except that 3-buteneal-diacetal is used instead of 3,3-diethoxy-1-propene.

Yield: 90%; $^1$H-NMR(CDCl$_3$, 300 MHz) δ 0.56(t, 2H), 1.08–1.17(m, 15H), 1.39(q, 2H), 1.55(q, 2H), 3.39(q, 2H), 3.54(q, 2H), 3.74(q, 6H), 4,.39(t, 1H); MS(m/z, relative intensity): 307(M$^+$–1, 40).

EXAMPLE 7

Preparation of 2-(1,3-dioxane)-2-yl)-ethyltriethoxysilane 2-(1,3-dioxane)-2-yl)-ethyltriethoxysilane is prepared using the same method as that of Example 4 except that 2-vinyl-1,3-dioxane prepared in Example 2 is used instead of 3, 3-diethoxy-1-propene.

Yield: 75%. $^1$H-NMR(CDCl$_3$, 300 MHz) δ 0.59(t, 2H), 1.16–2.24(m, 13H), 3.73–4.05(m, 10H), 4.41 (t, 1H); MS(m/z, relative intensity): 277(M$^+$–1, 3).

EXAMPLE 8

Preparation of 3-(1,3-dioxane)-2-yl)-propyltriethoxysilane 3-(1,3-dioxane)-2-yl)-propyltriethoxysilane is prepared using the same method as that of Example 4 except that 2-(2-propene-3-yl)-1,3-dioxane prepared in Example 3 is used instead of 3,3-diethoxy-1-propene.

Yield: 85%; $^1$H-NMR(CDCl$_3$, 300 MHz) δ 0.57(t, 2H), 1.19–2.10(m, 17H), 3.70–3.84(m, 6H), 4.04(m, 4H), 4.47(t, 1H); MS(m/z, relative intensity): 305(M$^+$–1, 9).

EXAMPLE 9

Preparation of polyvinyl alcohol-silane coupling agent

After 0.5 g of 3,3-diethoxypropyltriethoxysilane produced in Example 4 is dissolved in 5 ml of ethanol, 1 ml of 0.01 N sulfuric acid is added to the solution, and the mixture is allowed to react at room temperature for 2 hours. To this reactant, 50 g of 5% concentration polyvinyl alcohol (commercially available from Aldrich Co., weight. average molecular weight: 89,000 to 98,000, hydration degree: 99% or more) is added, the mixture is then allowed to react at room temperature for 2 hours, and then dried in an oven at 80° C. for 24 hours, thereby giving polyvinyl alcohol-silane coupling agent, a composite organic-inorganic material. The product is dissolved in DMSO-d$_6$ and then measured for an $^1$H-NMR spectrum. Results are shown in FIG. 5.

TEST EXAMPLES 1–10

To measure water solubility of a silane coupling agent with change in its weight, polyvinyl alochol-silane coupling agents, that are composite organic-inorganic materials, were prepared using silane coupling agents in the amounts ranging from zero to 625 ppm, according to the method of Example 9. The prepared materials were set forth as Test Examples 1 to 10 in Table 1 below.

50 ml of each of the prepared composite inorganic-organic materials different in weight of the silane coupling agent from each other is added to a Petri dish having a diameter of 8.5 cm, dried at a temperature of 80° C. under atmospheric pressure for 24 hours, and then further dried at a temperature of 120° C. for 1 hour. To measure water solubility, each of the composite organic-inorganic materials was dipped:in water at 60° C., and dried at 80° C. for 24 hours, and at 120° C. for 24 hours. At this time, each of the composite organic-inorganic material was measured for its weight before and after dipping in water. Measurements for the weight reduction (%) of the composite materials are set forth in Table 1 below.

TABLE 1

Water barrier property of composite organic-inorganic material with concentration of silane coupling agent

| Test Example | 5% Polyvinyl alcohol aqueous solution (ml) | Amount of silane coupling agent used (mg) | Weight reduction (%) of composite material |
|---|---|---|---|
| 1 | 50 | 0 | 86 |
| 2 | 50 | 25 | 59 |
| 3 | 50 | 75 | 37 |
| 4 | 50 | 125 | 31 |
| 5 | 50 | 175 | 23 |
| 6 | 50 | 250 | 9 |
| 7 | 50 | 325 | 8 |
| 8 | 50 | 400 | 6 |
| 9 | 50 | 500 | 4 |
| 10 | 50 | 625 | 4 |

As apparent from the above description, the present invention provides a silane coupling agent by which a composite organic-inorganic material is prepared in which a polymer and a silicon oxide are covalently bonded to each other. The composite organic-inorganic material prepared by the silane coupling agent is useful as a functional;material and coating, such as a surface-treating agent, an additive to organic synthetics, a metal protective coating, a structural coating, a fiber waterproof coating, and a coating for electronic parts.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. Silane coupling agent represented by the following formula I:

$R_1R_2R_3Si$—X wherein $R_1$, $R_2$, and $R_3$, respectively, represent straight or branched alkyl having 4 to 22 carbon atoms, alkoxy, phenyl, phenyl alkoxy, benzyloxy or phenyl alkyl group, each of these groups being substituted with a functional group selected from fluoride, glycidoxy, vinyl, (meth)acetyl, amino or mercapto group, with the proviso that at least one of $R_1$, $R_2$, and $R_3$ contain an alkoxy group;

X is an alkyl or arylalkyl group having 4 to 22 carbon atoms, each of these groups being substituted with at least one functional group selected from dioxoranyl, dioxanylalkyl, ketal, alkylideneketal, cycloalkylidenekatal, acetal, dialkylacetal, alkylideneacetal, phenylalkylideneacetal, benzylideneacetal, ketone, and cycloacetal having 4 to 8 carbon atoms and containing, in its carbon chain, at least one atom selected from oxygen, sulfur and nitrogen.

2. A method for preparing a silane coupling agent represented by the following formula I, comprising the steps of:
dissolving a vinyl derivative represented by the following formula II in a solvent under a nitrogen or argon atmosphere; and
reacting the resulting solution with an alkoxysilane derivative represented by the following formula III at a temperature of 20 to 200° C. for 1 to 72 hours in the presence of a metal catalyst to prepare the silane coupling agent of the formula I; or
comprising the steps of: dissolving alkylmagnesium halide represented by the following fomula IV in a solvent under a nitrogen or argon atmosphere; and
reacting the resulting solution with haloalkoxysilane represented by the formula V at a temperature of −78° C. to 50° C. for 0.1 to 5 hours to prepare the silane coupling agent of the formula I:

$R_1R_2R_3Si-X$     (I)

    (II)

$X-MgZ$     (III)

$R_1R_2R_3Si-Z$     (IV), and $H-SiR_1R_2R_3$     (V)

wherein $R_1$, $R_{21}$ and $R_3$, respectively, represent straight or branched alkyl having 4 to 22 carbon atoms, alkoxy, phenyl, phenyl alkoxy, benzyloxy or phenyl alkyl group, each of these groups being substituted with a functional group selected from fluoride, glycidyloxy, vinyl, (meth)acetyl, amino and mercapto groups, with the proviso that at least one of $R_1$, $R_2$, and $R_3$ contain an alkoxy group;

X is an alkyl or aryl alkyl group having 4 to 22 carbon atoms, each of these groups being substituted with at least one functional group selected from dioxoranyl, dioxanylalkyl, ketal, alkylideneketal, cycloalkylidenekatal, acetal, dialkylacetal, alkylideneacetal, phenylalkylideneacetal, benzylideneacetal, ketone, and cycloacetal having 4 to 8 carbon atoms and containing, in its carbon chain, at least one atom selected from oxygen, sulfur and nitrogen;

$Y_1$ is alkyl or arylalkyl group having 4 to 19 carbon atoms, each of these groups being substituted with at least one functional group selected from dioxoranylalkyl, dioxanylalkyl, ketal, acetal, dialkylacetal, alkylideneacetal, phenylalkylideneacetal, benzylideneacetal, ketone, and cycloacetal having 4 to 8 carbon atoms and containing, in its carbon chain, at least one atom selected from oxygen, sulfur and nitrogen;

$Y_2$ has a definition identical to that of $Y_1$, or may contain hydrogen atom; and Z is selected from F, Cl, Br, and I.

3. The method of claim 2, wherein the solvent is selected from the group consisting of lower alcohol having 1 to 10 carbon atoms, α-methylnaphtalene, methoxynaphtalene, chloronaphtalene, diphenylethane, ethyleneglycol, quinoline, benzene, nitrobenzene, chlorobenzene, bromobenzene, o-dichlorobenzene, toluene, dichlorotolune, xylene, chloroform, dichloromethane, tetrachlorocarbon, hexane, cyclohexane, heptane, octane, pentane, pyridine, dioxane, tetrahydrofuran (THF), furan, 2-methyl tetrahydrofuran, tetrahydropyran, pyrrole, dibromomethane, tetrachloroethane, 1,2-dichloroethane, 3-nitro-α,α,α-trifluorotoluene, diethylether, and petroleum ether.

4. The method of claim 2, wherein the metal catalyst is a complex compound in which a central metal is Pt, Ir, Os, Au, or As, and a ligand is H, F, Cl, Br, I, $PPh_3$, $C_5H_5$, CO, OH, $C_2H_4$, $CH_3$, $PCH_3$, $Si(CH_3)_3$, $C_5H_4(CH_3)$, $C_5H_3(CH_3)_5$, 1,5 cyclooctadiene, norbornadiene, $C_6H_5$, $CH_2$-t-Bu, acetylacetonato and a combination of two or more of these compounds.

5. The method of claim 2, wherein the metal catalyst is used in the amount of 1 to 1,000 ppm.

* * * * *